United States Patent
Solomito et al.

(10) Patent No.: US 8,184,838 B2
(45) Date of Patent: May 22, 2012

(54) CUSTOM-FIT HEARING DEVICE KIT AND METHOD OF USE

(75) Inventors: Joe A. Solomito, Lakeland, TN (US); George B. Kawell, Collierville, TN (US)

(73) Assignee: Radians, Inc., Bartlett, TN (US)

( * ) Notice: Subject to any disclaimer, the term of this patent is extended or adjusted under 35 U.S.C. 154(b) by 319 days.

(21) Appl. No.: 12/727,340

(22) Filed: Mar. 19, 2010

(65) Prior Publication Data
US 2010/0243513 A1 Sep. 30, 2010

Related U.S. Application Data

(62) Division of application No. 11/347,106, filed on Feb. 3, 2006, now Pat. No. 7,715,572.

(60) Provisional application No. 60/650,239, filed on Feb. 4, 2005.

(51) Int. Cl.
*H04R 25/00* (2006.01)
(52) U.S. Cl. .......................................... 381/322; 381/72
(58) Field of Classification Search ................. 381/23.1, 381/72, 322, 324, 328, 380–381; 128/864, 128/867; 29/896.21
See application file for complete search history.

(56) References Cited

U.S. PATENT DOCUMENTS

| | | |
|---|---|---|
| 3,344,220 A | 9/1967 | Cook |
| 3,440,314 A | 4/1969 | Frisch |
| 3,897,376 A | 7/1975 | Lampe |
| 3,925,277 A | 12/1975 | Lampe |
| 4,712,245 A | 12/1987 | Lyregaard |
| 5,006,055 A | 4/1991 | Lebisch et al. |
| 5,131,411 A | 7/1992 | Casali et al. |
| 5,333,622 A | 8/1994 | Casali et al. |
| 5,455,994 A | 10/1995 | Termeer et al. |
| 5,804,109 A | 9/1998 | Perkins |
| 6,339,648 B1 | 1/2002 | McIntosh et al. |
| 6,754,357 B2 | 6/2004 | McIntosh et al. |
| 2002/0076057 A1 | 6/2002 | Voix |
| 2002/0114479 A1 | 8/2002 | McIntoch et al. |
| 2003/0112990 A1 | 6/2003 | McIntosh et al. |
| 2005/0224082 A1 | 10/2005 | Johnson |

OTHER PUBLICATIONS http://www.earinc.com (4 pages).
http://www.sbmedco.com/mold_kit.asp (2 pages).

*Primary Examiner* — Suhan Ni
(74) *Attorney, Agent, or Firm* — Womble Carlyle Sandridge & Rice, LLP

(57) ABSTRACT

A kit for preparing a custom-fit ear protection molding is provided having a first container containing a compliant material and a second container containing a hardening agent such that when the compliant material and the hardening agent are combined and kneaded, a resulting compound is formed which may be inserted into the ear of a user and allowed to cure. A method of affecting the hearing of a user is provided. A method of selling a hearing-protection kit is also provided along with a method of manufacturing the disclosed kit.

6 Claims, 4 Drawing Sheets

CUSTOM-FIT HEARING DEVICE KIT AND METHOD OF USE

CROSS REFERENCE TO PROVISIONAL APPLICATIONS

The present application is a divisional application of U.S. Ser. No. 11/347,106 filed Feb. 3, 2006, which claims the benefit of U.S. Provisional Patent Application No. 60/650,239, filed Feb. 4, 2005, each of which are incorporated herein in their entirety.

BACKGROUND OF THE INVENTION

1. Field of the Invention

The present invention relates generally to hearing protection devices. More particularly, the present invention relates to a kit and method for custom-molding a compound to the contours of a user's ear.

2. Description of the Related Art

There are a number of available in-ear hearing-protection devices available. For example, U.S. Pat. No. 5,333,622 discloses a hearing-protection device that defines a cylindrical-shaped, soft foam material. The foam material may be compressed and then inserted into the ear canal of a user. The foam decompresses and leaves a relatively snug-fitting and disposable hearing protection device. In another instance, U.S. Pat. No. 3,925,277 offers a hearing-protection device comprised of a compliant, soft rubber material that conforms to the shape of the ear canal of a user upon insertion. The rubber ear plug may be reused a number of times before disposal.

Each of these ear plugs is relatively inexpensive and easy to use. At the same time, each of these types of plugs is non-custom fitted or "off the shelf," and may be uncomfortable. More importantly, these plugs do not typically provide the level of hearing protection or comfort available in a custom-fit, hearing-protection device due to improper fit or use. Further still, these ear devices do not accommodate electrical instruments such as mobile phone ear pieces or earbuds.

Custom-fit hearing-protection devices are available. One example is the E.A.R. Custom Electronic Earplug Series offered by Ear, Inc. The E.A.R. Custom Electronic Earplug comprises an electronic attenuator and a custom-fit housing. To custom-fit the housing to an ear, an ear mold template is first taken by a doctor or audiologist. The mold is then shipped to a manufacturer for construction of the custom-fit, electronic earplug. This custom-fit option may provide more comfort and greater hearing protection than non-custom hearing protectors. However, the process is expensive for a number of reasons, including the additional step of the doctor or audiologist creating the ear mold. Additionally, because of the steps involved, the process may take a number of days (or weeks) to complete, leaving the purchaser in a position of using a non-custom earplug while waiting on receiving the custom device.

The non-electronic Insta-Mold 20 Earplugs provides an example of a custom-fit hearing protection device. This product also is created by a hearing device professional, and involves the appurtenant time and expense.

Therefore, there is a need for a custom-fit, hearing device that does not require fitting by a hearing professional, but may be constructed from a kit purchased by the end user. The kit may optionally include an electronic instrument such as an ear bud, a noise filter, or an amplifier. Further, there is a need for a custom-fit hearing device that may be constructed by the user in a short period of time.

SUMMARY OF THE INVENTION

A hearing device kit is first provided. In one embodiment the kit includes a first container containing a compliant material, and a second container containing a hardening agent such that when the compliant material and the hardening agent are combined and kneaded, a resulting compound is formed which may be inserted into the ear of a user and allowed to cure. Instructions for instructing the user as to the formation of the compound and the creation of a hearing device may also be included.

In one aspect, the hearing device kit may have sufficient compliant material and hardening agent for creating a compound sufficient to form a hearing device for two ears, that is, both of user's ears.

In another aspect, the kit may include a pair of electronic instruments such as earbuds or hearing attenuators.

In yet another aspect, the kit's packaging may include an SKU identifier.

A method of affecting the hearing of a user is also provided. In one embodiment, the method includes the step of opening a kit having a first molding material comprising a compliant material, a second molding material comprising a hardening agent, instructions for instructing the user on combining the first and second molding materials, and an SKU identifier. The method also includes the steps of combining the first and second molding materials to form a molding compound, kneading the molding compound, pressing a first portion of the molding compound into a first ear so as to closely conform the compound to the contours of both the inner canal and outer orifice portions of the first ear, shaping the exposed molding compound, waiting a period of time for the molding compound to cure, and removing the cured molding compound from the first ear. The above-recited steps may be repeated for a second ear.

In one aspect, the method of affecting the hearing of a user may include the steps of inserting an electronic instrument into the first ear of the user and forming the molding compound around the electronic instrument prior to hardening so as to secure the electronic instrument in the mold and reduce ambient noise.

In yet another aspect, the method of affecting the hearing of a user may include the steps of flattening the first portion of the molding compound after it is kneaded, forming a through-opening within the flattened compound, and positioning an electronic instrument in the through-opening. The step of forming the molding compound around the electronic instrument is also provided. Alternatively, the step of pressing a first portion of the molding compound into a first ear comprises pressing the first portion of the molding compound and electronic instrument into the first ear, essentially together.

The electronic instruments may be one or a pair of attenuators, earbuds, radio receivers, mobile phone earpieces or amplifiers. The molding compound may be a viscous silicon rubber.

A method of selling a hearing-protection kit is also provided. In one embodiment, the method includes the step of receiving a pre-packaged custom-molding compound kit, the kit comprising a first material representing a compliant material, a second material representing a hardening agent for the compliant material, and an SKU identifier. The compliant material may be comprised of a siloxane while the hardening agent may be comprised of an alkyl silicate and curing catalyst. The method also includes the step of placing the kit in a retail setting for user inspection. In addition, the step of scanning the SKU identifier for sale to a retail customer is provided. The kit may contain a pair of electronic instruments such as a pair of attenuators, earbuds, radio receivers, or amplifiers.

A method of manufacturing a hearing kit is also provided. In one embodiment, the method includes the step of providing a first material comprising a compliant material. The method also includes the step of providing a second material comprising a hardening agent such that when the compliant material and the hardening agent are combined and kneaded, a resulting compound is formed which may be inserted into the ear of a user and allowed to cure. The method also provides inserting the first material and second material into separate containers and packaging the containers into an enclosure for sale to an end user. In addition, the step of packaging instructions for instructing an end user as to the formation of the compound is provided. The kit may contain sufficient compliant material and hardening agent to allow an end user to create a compound sufficient to form a hearing device for substantially two ears.

In another aspect, the method of manufacturing a hearing kit may include the additional step of placing a pair of electronic instruments into the enclosure. The electronic instruments may be an attenuator, earbud, radio receiver, or an amplifier.

BRIEF DESCRIPTION OF THE DRAWINGS

So that the manner in which the above recited features of the present invention can be better understood, certain drawings or flow charts are appended hereto. It is to be noted, however, that the appended illustrations depict only selected embodiments of the inventions and are therefore not to be considered limiting of scope, for the inventions may admit to other equally effective embodiments and applications.

DETAILED DESCRIPTION

Definitions

As used herein, the term "high decibel activity" includes, but is not limited to, shooting fireworks, hunting, firearm sports, factory environments, assembly line environments, farming enterprises, military maneuvers, construction work, fire/police services, airport services, automotive sports and exhibitions, concerts, snoring and any other activity or event where loud noise suppression and/or noise amplification may be recommended.

As used herein, the term "user" refers to an individual who seeks to use a hearing device.

The term "electronic instrument" includes, but is not limited to, attenuators, amplifiers, speakers, sound filters, radio receivers, earbuds, or any combination thereof. The term "earbud" refers to any ear piece for delivering sound from an electronic device such as a radio, a portable telephone, a CD player, a mobile phone, a satellite system, or other device.

The term "SKU" refers to a stock unit. As used herein, "SKU" includes, but is not limited to, any unique identifier used to refer to a specific product in inventory or in a catalog. Non-limiting examples include a bar code, a magnetic strip, a scannable chip, a product number, or other product identification means.

Description of Specific Embodiments

Figure 1:
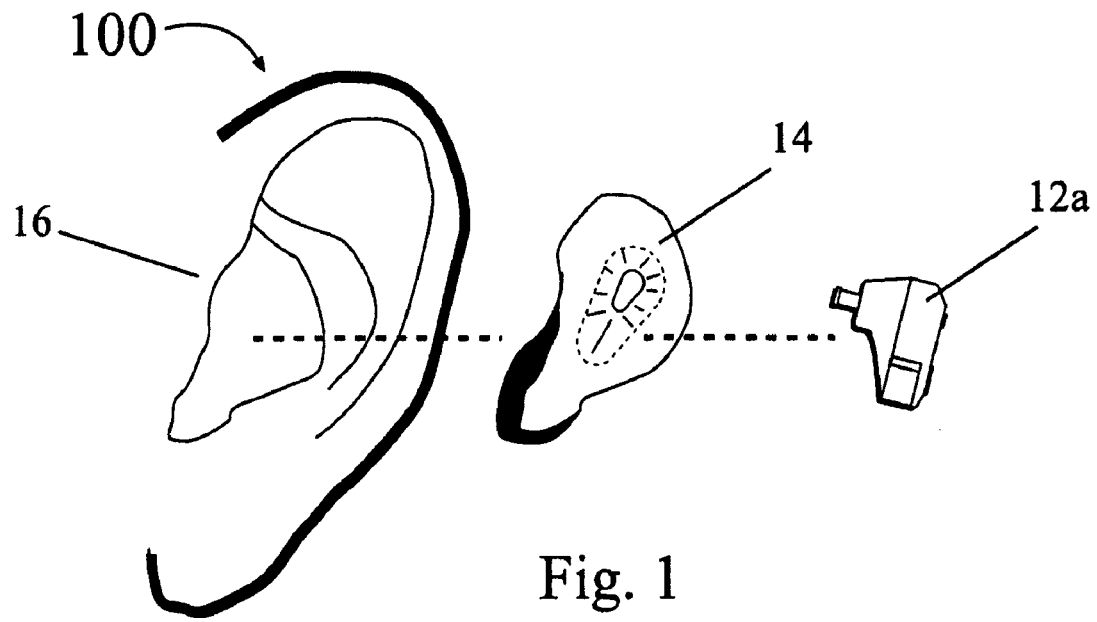
FIG. 1 presents a perspective view of a custom-molded hearing device that has been constructed from a kit in accordance with the present invention. The hearing protection device is exploded away from the user's ear. Further, an optional electronic hearing instrument is exploded away from the device.

FIG. 1 presents a perspective view of a custom-molded hearing device 100. The hearing device has been constructed from a kit (such as kit 200 of FIG. 2). The illustrative hearing device 100 comprises a custom-molded plug 14 for placement into an ear 16. The device 100 further includes an optional electronic hearing instrument 12a. In the view of FIG. 1, the plug 14 is exploded away from the ear 16 while the electronic instrument 12a is exploded away from the plug 14.

Figure 2:
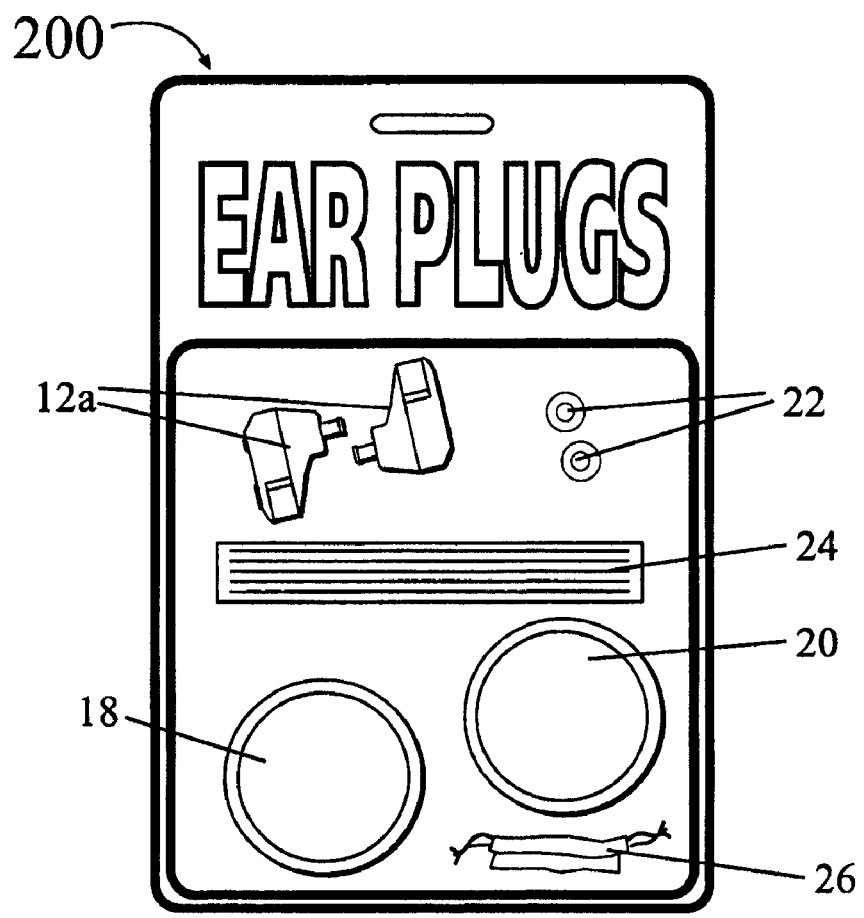
FIG. 2 presents a front view of an embodiment of a kit for custom-molding the hearing device of FIG. 1. A pair of electronic instruments is provided in the kit.

FIG. 2 presents a front view of an embodiment of a kit 200 for custom molding the inventive hearing device 100 of FIG. 1. The kit 200 is sold or otherwise supplied to an end user. The kit 200 includes two small containers 18 and 20 containing a two-part molding material. Further, the kit 200 comprises a pair of optional electronic instruments 12a. A pair of batteries 22 may be included in the kit 200. In addition, instructions 24 for custom molding the hearing device 100 are preferably included. Other related items such as a case 26 for holding any molded plug 14 may also be included.

It is noted that the kit embodiment 200 in FIG. 2 includes duplicate parts for constructing a pair of hearing devices 100. In this way, a user may create separate hearing devices 100 for each ear 16. Containers 18 and 20 will preferably include enough compound-forming material to create two separate plugs 14. Alternatively, kit 200 may include two sets of containers 18 and 20 containing a two-part molding material, each set proportioned to make a finished plug 14 for a respective ear 16.

The contents of container 18 may include a crosslinkable polymer such a silicone putty. The contents of container 20 may include a hardening agent comprised, for example, of an alkyl silicate or partially hydrolyzed alkyl silicate and a catalyst. The contents of container 18 and 20 are combined to form a molding compound which hardens or cures over a period of time.

In one aspect, the crosslinkable polymer of container 18 may be a silicon-based polymer such as a siloxane. The alkyl silicate of container 20 may be a non-ionic organosilicate. The catalyst of container 20 may be a metallic salt of an organic carboxylic acid.

In another aspect, the molding material is comprised of the two-part, non-toxic, silicone-putty molding material known as "Knead A Mold" supplied by A2Z Solutions, Inc. of Chattanooga, Tenn. A first material, which may be included in container 18, comprises a viscous, odorless white or tan putty. A second material, which may be an odorless, purple putty may be included in container 20. More specifically, the "Knead A Mold" compound may comprise a material having a silicon-based polymer such as a organopolysiloxane. More information about each part comprising the two-part Room Temperature Vulcanizing (RTV) silicone organopolysiloxane may be supplied by each parts' respective material data safety sheets (MSDS), which are hereby incorporated by reference in their entirety.

When the contents of containers 18 and 20 are first combined, the resulting molding compound is easily shapeable and non-tacky. The molding compound is designed to slowly harden over a period of time (e.g. up to ten or eleven minutes) giving the user ample time to insert the electronic instrument 12a in the molding compound (if desired), and/or press the molding compound into the ear canal to cure into a custom molding.

Turning now to the electronic instrument 12a, the electronic instrument 12a may be any number of instruments including, but not limited to, a sound filter, radio receiver (and speaker), amplifier, attenuator, or combination amplifier and attenuator, for example. In one embodiment of kit 200, an electronic instrument 12a is comprised of an electronic amplifier/attenuator device sold by Taising Electronics Industrial Ltd., of Hong Kong, China, as part number TS-2388 or TS-2386. The instrument 12a may include various features such as a microphone, a volume control, an on/off switch, and tone control (not specifically shown).

In the case that an electronic instrument 12a comprises a combined amplifier/attenuator device, electronic instrument 12a may be configured to amplify sounds under a predetermined decibel level and attenuate sounds over a predetermined decibel level. This amplifier/attenuator configuration preferably allows the user to hear sounds which are not damaging to the ear (e.g. voice conversations, the rustling of leaves when hunting, etc.), while maintaining the ability to attenuate potentially damaging sounds (e.g. gun shots).

In one embodiment, electronic instrument 12a is configured to amplify sounds up to an OSHA recommended maximum allowable decibel level of 85 decibels. Additionally, the instrument attenuates (compresses) sound above a level of 85 decibels to a safe, comfortable level. In some embodiments, the amplification/attenuation properties of electronic instrument 12a may be user configurable (e.g. through a knob or dip switches). At least one battery 22 for an electronic instrument 12a may also be supplied, if needed, which may be a hearing-aid type battery (e.g. type A3 12).

Figure 3:
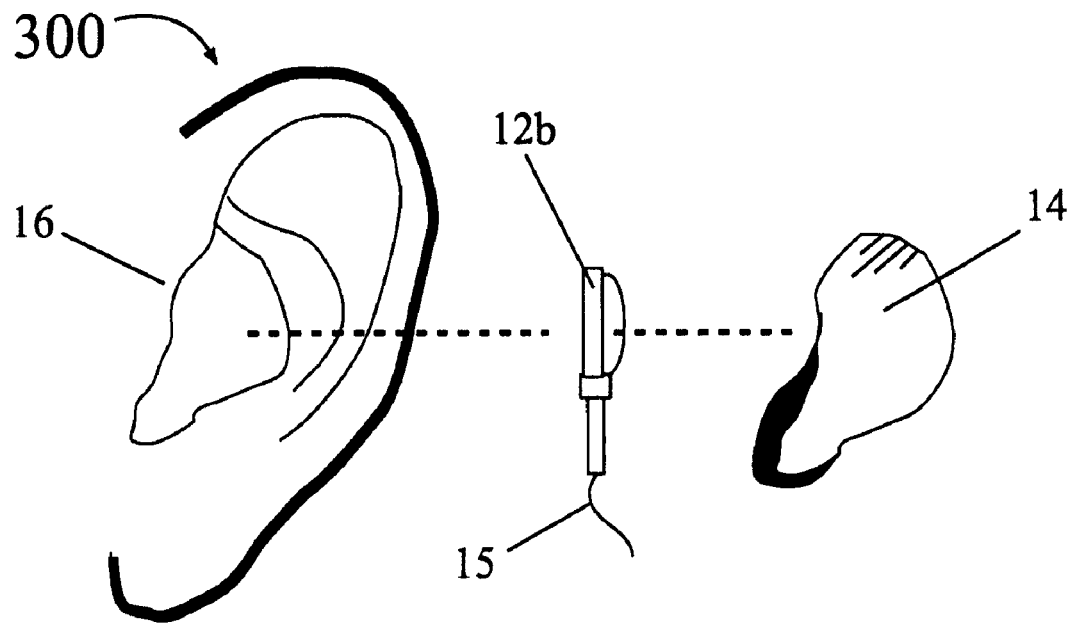
FIG. 3 presents a perspective view of the custom-molded hearing device of FIG. 1. Here, a plug is exploded away from an earbud. The earbud, in turn, is exploded away from the user's ear.

FIG. 3 presents an exploded view of an alternative embodiment of a hearing device 300. In this embodiment, the hearing device 300 comprises an electronic instrument 12b and a custom-molded plug 14 for placement into the contours of an ear 16 surrounding the electronic instrument 12b. The plug 14 is exploded away from the electronic instrument 12b. The electronic instrument 12b, in turn, is exploded away from the user's ear 16.

The molded plug 14 is the same type of moldable material as would be used in the kit 200 of FIG. 2. This allows a user to create a custom-fit hearing device 300 which not only secures an electronic instrument 12b in the ear 16, but also reduces the entry of outside, ambient noise. The hearing of the user is thus protected as a result of the lower required listening volume.

In the embodiment of FIG. 3, the electronic instrument 12b is a small speaker known as an "earbud." The earbud covers the ear canal of the user's ear 16. The earbud may be adapted to communicate with any number of electronic devices for producing sound such as a Walkman®, a digital audio player (DAP), an iPod®, a portable phone, and/or a cellular phone, for example.

Figure 4:
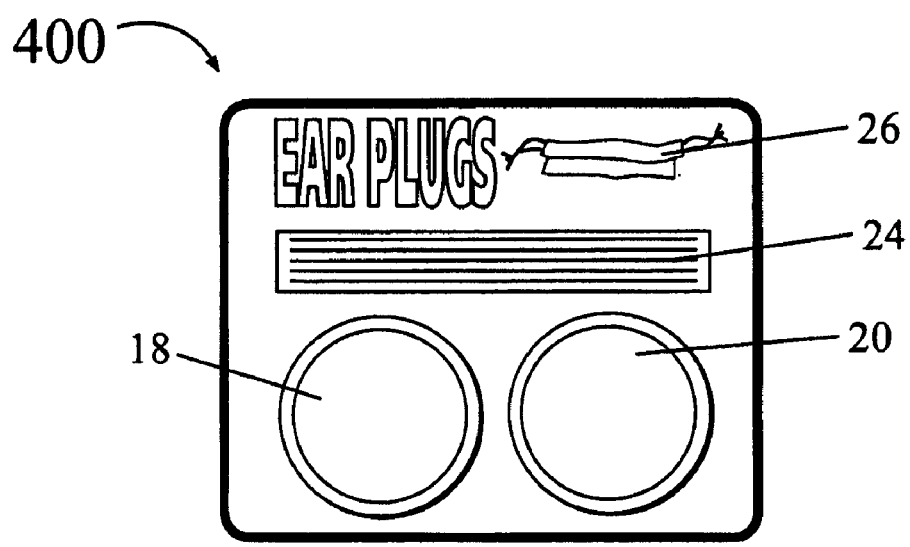
FIG. 4 presents a front view of an embodiment of a kit for custom-molding the hearing device of FIG. 3. In this kit, the electronic instrument is not provided, but is supplied by the user.

FIG. 4 presents a front view of an embodiment of a kit 400 for custom-molding the hearing device 300 of FIG. 3. The kit 400 may be supplied to the end user with any of: two small containers 18 and 20 containing the two-part molding material described in FIG. 2, instructions 24 for custom molding the hearing protection device 300, and a case 26 for holding any molded plugs 14. Some embodiments of the kit 400 may include duplicate parts for constructing more than one hearing-protection device 300. In some embodiments, kit 400 may again include two sets of containers 18 and 20 containing two-part molding material, each set proportioned to make a finished hearing device 300 for each ear.

It is noted that the kit 400 of FIG. 4 does not include the earbud 12b. The earbud 12b is typically provided by the user from a previously purchased electronic instrument such as a Walkman®, a digital audio player (DAP), an iPod®, a portable phone, and/or a cellular phone, for example. The electronic instrument 12b of FIG. 3 includes a wire 15 for connecting to or plugging into the separate electronic instrument (not shown).

Figure 5:
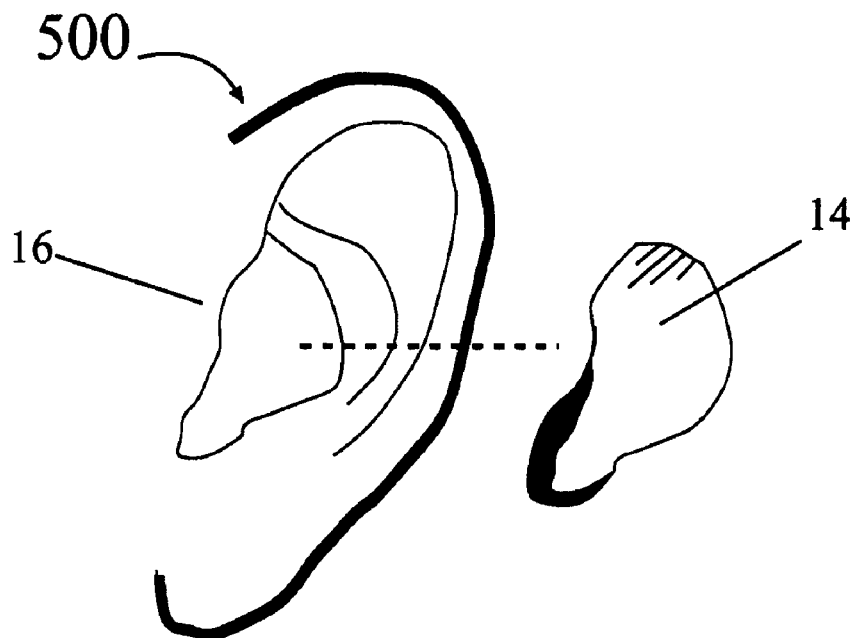
FIG. 5 presents a perspective view of a custom-fit hearing-protection device. The device is exploded away from a user's ear. Here, no electronic instrument is used.

FIG. 5 presents a perspective view of an embodiment for a hearing device. In this embodiment, the hearing device 500 is a hearing-protection device, and comprises a custom-molded plug 14 for placement into the contours of the user's ear 16. The hearing-protection device 500 is used primarily to reduce the entry of noise produced while the user is engaging in a high decibel activity. The custom-molded plug 14 may have a Noise Reduction Rating of at least 26 decibels.

Figure 6:
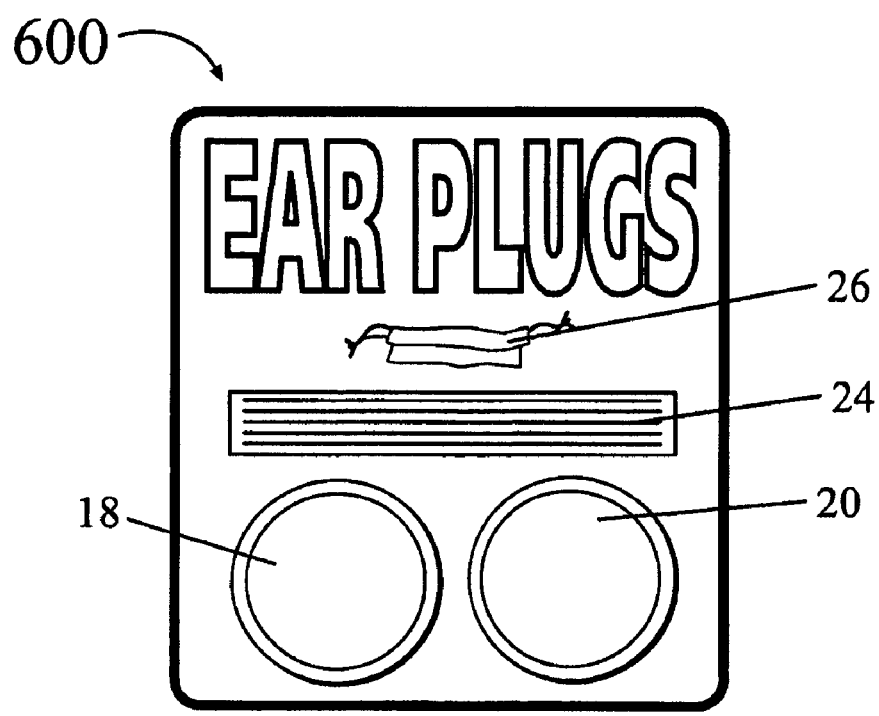
FIG. 6 presents a front view of an embodiment of a kit for custom-molding the hearing-protection device used in FIG. 5.

FIG. 6 presents a front view of an embodiment of a kit 600 for custom-molding the hearing-protection device 500 as depicted in FIG. 5. The kit 600 may be supplied to the end user with any of: two small containers 18 and 20 containing the two-part molding material described in FIG. 2, instructions 24 for custom molding the hearing protection device 500, and a case 26 for holding the finished plugs. Some embodiments of the kit 600 may include duplicate parts for constructing more than one hearing-protection device 500. In some embodiments, kit 600 may include two sets of containers 18 and 20 containing two-part molding material, each set proportioned to make a finished hearing protection device 500 for each ear. The kit 600 will have packaging that includes an SKU identifier.

Figure 7:
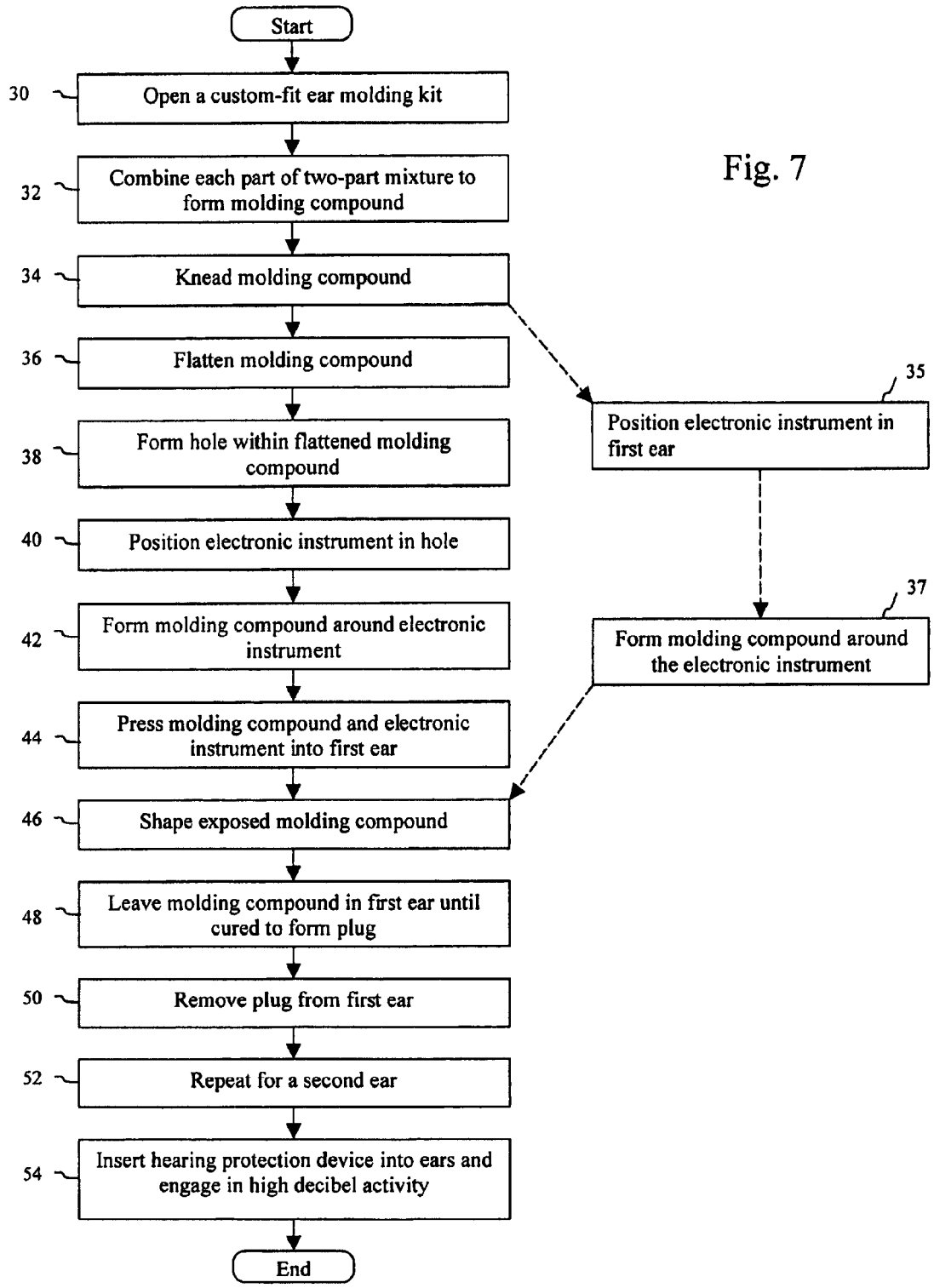
FIG. 7 depicts a flow chart representing illustrative steps performed to custom-fit a hearing device.

Various kits 200, 400, 600 have been described herein. The present inventions also include methods for using such kits 200, 400, 600 to provide a hearing device such as devices 100, 300, or 500 to a user. FIG. 7 depicts a flow chart of a method for custom molding a hearing device 100, 300, or 500 from the parts contained in any of kits 200, 400, 600, respectively. For the sake of simplicity, the electronic instruments 12a, 12b are generically referred to as "12."

At step 30, the end user opens a previously purchased custom-fit molding kit having the containers 18 and 20 comprising the two-part molding material described above. In step 32, a portion of each part is mixed to form a molding compound. At step 34, the molding compound is then thoroughly kneaded. Each part of the two-part molding material is preferably a different color. In this way, a consistent color of the molding compound may be used as an indicator that the compound has been adequately kneaded. A variety of colors may be used with each part of the two-part mixture may be dyed to provide a specific desirable color for the finished device.

Before pressing the molding compound into an ear 16, an electronic instrument 12 may be pressed into the molding material, or the molding material may be shaped around the electronic instrument 12 after insertion into an ear 16. In one embodiment, at step 36, the molding compound may be flattened to a size and shape sufficient to cover at least the front and sides of an electronic instrument 12. For example, for the described electronic instruments (part nos. TS-2388 or TS-2386) the molding compound may be shaped to approximately the size of a U.S. quarter dollar. At step 38, a hole is formed to insert the electronic instrument 12. For example, for the described electronic instruments 12, the hole may be approximately ⅛" in diameter and may be formed in a portion, such as the central portion, of the flattened molding compound. At step 40, an electronic instrument 12 is positioned in the hole such that the outside of the electronic instrument 12 remains exposed. At step 42, the molding compound is formed around the sides of the electronic instrument 12. At step 44, the molding compound, with the electronic instrument 12 installed; may be carefully pressed into the ear orifice of the intended user such that the molding compound conforms closely with the contours of the ear canal and exterior portions of the ear to form a seal.

In some cases it may be helpful to press around the edges of the exposed portions of the molding compound to assist in creating a consistent seal with the ear 16 of the user. In the case that the intended user is performing the molding steps, it may be helpful to use a mirror to visually ensure the proper seal.

Once a seal is established, at step 46, any exposed molding compound may be shaped to form a consistent, finished look. At step 48, the molding material with electronic instrument 12 is kept in the ear while the molding material cures to a semirigid yet flexible state. The cure time may be up to eleven minutes. However, this is only an example, and the cure time may vary widely on the type of molding mixture used, the mixture ratio of the two-components, and/or environmental conditions. While a short cure time is generally desirable, it is also be desirable that the cure time allows enough time to insert the electronic instrument 12 and/or press the mixture into an ear 16 before a substantial hardening is achieved.

The cured molding compound forms a custom-molded plug 14. At step 50, the custom-fit hearing device (FIGS. 1, 3, 5) may be removed from the ear 16. An independent lab may be used to verify the noise reduction rating (NRR) on a completed sample.

At step 52, steps 38-48 may be repeated for an additional ear. The custom molded plugs 14 may be stored for protection in a supplied convenient case 26. Finally, at step 54, a user may insert a hearing protection device (FIGS. 1, 3, 5) into an ear and engage in a high decibel activity. In another instance, the user may choose to engage in an activity requiring the amplification of outside noise. In this case, the electronic instrument 12 is an amplifier.

In alternative embodiment of the method, steps 36-44 may be replaced with two alternative steps. More specifically, after step 34, the user may position an electronic instrument in an ear 16 at step 35. Next, in step 37, the user may form the molding compound around an electronic instrument 12 while the instrument 12 is positioned in an ear 16 so as to secure the instrument 12 in the ear 16 and reduce entry of outside, ambient noise.

In the case that the kit (FIG. 4, 6) does not include an electronic instrument 12 or the user does not wish to use an electronic instrument, several steps for molding the hearing device may be skipped or slightly altered. For example, steps 36 through 44 which include: flattening the molding compound, inserting a hole in the flattened mixture, positioning the speaker within the hole wrapping the sides around the electronic instrument 12, and pressing the molding compound with the electronic instrument into an ear 16 are not applicable to forming a non-electronic hearing protection device. Rather, after step 34, the molding compound may be formed into a shape having at least one end sized and shaped for insertion into a portion of an ear canal and one larger end for creating a seal on the exterior of an ear orifice.

For example, the molding compound may be formed (e.g. rolled) into a generally conical shape (having one end larger than the other), and pressed into an ear canal. The narrow end of the molding compound may be inserted into an ear canal and pressed into the ear while the larger end of the molding compound, protruding from the ear orifice, is carefully formed to provide a seal with an ear, as described in step 44 above. Any exposed molding compound may be shaped to form a consistent, finished look, as described in step 46. Finally, the molding compound is cured in an ear 16 as in step 48.

A method of selling a hearing-protection kit is also provided (not shown). In one embodiment, a retail or wholesale dealer receives a pre-packaged custom-molding compound kit having a first material representing a compliant material, a second material representing a hardening agent for the compliant material, and an SKU identifier. The compliant material may be comprised of a siloxane while the hardening agent may be comprised of an alkyl silicate and curing catalyst. The kit is then displayed in a retail setting for user inspection and sold to an end user upon scanning the SKU identifier on the kit packaging. The kit may contain a pair of electronic instruments such as a pair of attenuators, earbuds, radio receivers, or amplifiers.

A method of manufacturing a hearing kit is also provided (not shown). In one embodiment, the method includes the step of providing a first material comprising a compliant material. The method also includes the step of providing a second material comprising a hardening agent such that when the compliant material and the hardening agent are combined and kneaded, a resulting compound is formed which may be inserted into the ear of a user and allowed to cure. The manufacturer then places the first material and second material into separate containers and packages the containers into an enclosure for sale to an end user. In addition, the manufacturer may include instructions for instructing an end user as to the formation of the compound is provided. The kit may also contain sufficient compliant material and hardening agent for creating a compound sufficient to form a hearing device for substantially two ears.

In another aspect, the manufacturer may place a pair of electronic instruments into the enclosure. The electronic instruments may be an attenuator, earbud, radio receiver, or an amplifier.

It should again be understood that the disclosed embodiments are merely exemplary of the inventions, which may be embodied in various forms. It is intended that all alternatives, modifications and equivalents as may be included within the spirit and scope of the invention as defined by the appended claims. Therefore, the details disclosed herein are not to be interpreted as limiting, but merely as the basis for the claims and as a basis for teaching one skilled in the art how to make and/or use the invention.

We claim:

1. A hearing device kit, comprising:
   a first container containing a compliant material;
   a second container containing a hardening agent such that when the compliant material and the hardening agent are combined and kneaded, a resulting compound is formed which may be inserted into the ear of a user and allowed to cure; and
   optionally, instructions for instructing the user as to the formation of the compound and the creation of a hearing device.

2. The kit of claim 1, wherein sufficient compliant material and hardening agent are provided for creating a compound sufficient to form a hearing device for essentially two ears.

3. The kit of claim 2, further comprising packaging that has an SKU identifier thereon.

4. The kit of claim 1, wherein the compliant material is a silicone putty;

and the hardening agent is a silicate.

5. A method of affecting the hearing of a user, comprising the steps of:

opening a kit, the kit comprising;
- a first molding material comprising a compliant material,
- a second molding material comprising a hardening agent,
- optionally, instructions for instructing the user on combining the first and
- second molding materials, combining the first and second molding materials to form a molding compound;

kneading the molding compound;

pressing a first portion of the molding compound into a first ear;

shaping the exposed molding compound;

waiting a period of time for the molding compound to cure; and removing the cured molding compound from the first ear.

6. The method of claim 5, further comprising the step of:

pressing a second portion of the molding compound into a second ear;

shaping the exposed molding compound;

waiting a period of time for the molding compound to cure; and removing the cured molding compound from the second ear.

* * * * *